(12) United States Patent
Pyayt

(10) Patent No.: US 9,547,899 B1
(45) Date of Patent: Jan. 17, 2017

(54) MOBILE HEMOLYSIS DETECTION IN WHOLE BLOOD SAMPLES

(71) Applicant: Anna Pyayt, Tampa, FL (US)

(72) Inventor: Anna Pyayt, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/873,978

(22) Filed: Oct. 2, 2015

Related U.S. Application Data

(60) Provisional application No. 62/060,816, filed on Oct. 7, 2014.

(51) Int. Cl.
| | |
|---|---|
| *G06K 9/00* | (2006.01) |
| *G06T 7/00* | (2006.01) |
| *G06K 9/62* | (2006.01) |
| *G06K 9/46* | (2006.01) |
| *H04N 5/225* | (2006.01) |
| *G06T 7/40* | (2006.01) |
| *A61B 5/00* | (2006.01) |

(52) U.S. Cl.
CPC ......... *G06T 7/0012* (2013.01); *G06K 9/00134* (2013.01); *G06K 9/4652* (2013.01); *G06K 9/6202* (2013.01); *G06T 7/408* (2013.01); *H04N 5/2256* (2013.01)

(58) Field of Classification Search
USPC ............... 382/100, 103, 106–107, 128–134, 140,382/162–168, 173, 181, 190, 199, 209, 219,382/224, 232, 254, 274, 276, 286, 291, 305,382/312; 506/9; 600/322; 494/10; 422/82.05; 436/169
See application file for complete search history.

(56) References Cited

U.S. PATENT DOCUMENTS

| | | | | |
|---|---|---|---|---|
| 5,416,026 | A * | 5/1995 | Davis ................... | G01N 33/725 436/169 |
| 7,790,464 | B2 * | 9/2010 | Tarasev ................ | G01N 33/721 422/82.05 |
| 8,114,003 | B2 * | 2/2012 | Green ................. | A61M 1/3693 494/10 |
| 8,571,619 | B2 * | 10/2013 | Al-Ali ................ | A61B 5/14551 600/322 |

(Continued)

FOREIGN PATENT DOCUMENTS

| | | |
|---|---|---|
| WO | 2013085462 A1 | 6/2013 |
| WO | 2013188686 A3 | 12/2013 |
| WO | 2014159193 A1 | 10/2014 |

OTHER PUBLICATIONS

Roberts. Endothelial dysfunction in preeclampsia. Seminars in reproductive endocrinology. 1998. 5-15.

(Continued)

*Primary Examiner* — Seyed Azarian
(74) *Attorney, Agent, or Firm* — Nilay J. Choksi; Smith & Hopen, P.A.

(57) ABSTRACT

A system for hemolysis detection, where the system generally includes—individually or in combination—a containment apparatus for holding the blood sample and a software application for analyzing the blood sample. The containment apparatus houses the sample therein, and blocks out any light from penetrating the apparatus and reflecting off of the sample. In conjunction, the software application uses camera color for processing the color of the sample to determine the hemoglobin level in plasma based on the color.

16 Claims, 21 Drawing Sheets
(21 of 21 Drawing Sheet(s) Filed in Color)

(56) References Cited

U.S. PATENT DOCUMENTS

2012/0309636 A1* 12/2012 Gibbons ............ H04N 5/23222
506/9

OTHER PUBLICATIONS

Habli and Sibai. Chapter 16: Hypertensive disorders of pregnancy. Danforth's Obstetrics and Gynecology. 2008: p. 257-275.
Choudhury and Mathur. Visual detection of hemolysis in a blood bag before issue. Asian J. Transfusion Science. 2011. vol. 5 (No. 1): 61-62.
Rother et al., The clinical sequelae of intravascular hemolysis and extracellular plasma hemoglobin: A novel mechanism of human disease. JAMA. 2005. vol. 293 (No. 13): 1653-1662.
Rosse. Paroxysmal nocturnal hemoglobinuria—present status and future prospects. West J Med. 1980. vol. 132 (No. 3): p. 219-228.
Simundic et al., Hemolysis detection and management of hemolyzed specimens. Biochem Med. 2010. vol. 20 (No. 2): 154-159.
Hartmann et al., Paroxysmal nocturnal hemoglobinuria: clinical and laboratory studies relating to iron metabolism and therapy with androgen and iron. Medicine. 1996. vol. 45 (No. 5): 331-363.

* cited by examiner

MOBILE HEMOLYSIS DETECTION IN WHOLE BLOOD SAMPLES

BACKGROUND OF THE INVENTION

1. Field of the Invention

This invention relates to mobile applications. Specifically, the invention relates to mobile applications for hemolysis detection.

2. Brief Description of the Prior Art

Prenatal conditions are the fourth leading cause of death in developing nations and still pose significant health risks in countries with high income. Preeclampsia is a prenatal complication associated with high blood pressure and organ failure, which can result in potential maternal and/or fetal compromise and/or loss (Roberts, J. M. "Endothelial dysfunction in preeclampsia. Seminars in reproductive endocrinology". 1998. GEORG THIEME VERLAG; Habli, M. and B. Sibai. "Hypertensive disorders of pregnancy". *Danforth's Obstetrics and Gynecology,* 2008: p. 257-275). Globally, preeclampsia and other hypertensive disorders of pregnancy are a leading cause of maternal and infant illness and death. Its complications are the reason for 25% of maternal deaths worldwide in addition to fetal and neonatal death. By conservative estimates, these disorders are responsible for 76,000 maternal and 500,000 infant deaths each year. Preeclampsia can rapidly escalate to a dangerous complication known as HELLP syndrome. What is needed is a mechanism of detecting the first signs of this deadly complication while the mother is still stable and the baby can be promptly delivered, since this is the only opportunity to save their lives.

According to the Preeclampsia Foundation, the mortality rate of HELLP syndrome has been reported to be as high as 25%. HELLP syndrome can be difficult to diagnose, especially when high blood pressure and protein in the urine are not present. Its symptoms are sometimes mistaken for gastritis, flu, acute hepatitis, gall bladder disease, or other conditions. Among pregnant women in the United States, about 5% to 8% develop preeclampsia. It is estimated that about 15% of those women will develop evidence of HELLP syndrome. This mean as many as 48,000 women per year will develop HELLP syndrome in the U.S.

Most often, the definitive treatment for women with HELLP Syndrome is the delivery of their baby. During pregnancy, many women suffering from HELLP syndrome require a transfusion of some form of blood product (red cells, platelets, plasma). Corticosteroids can be used in early pregnancy to help the baby's lungs mature. Some healthcare providers may also use certain steroids to improve the mother's outcome, as well.

Overall, perinatal mortality from HELLP Syndrome (stillbirth plus neonatal death) ranges from about 7.7% to 60%. Most of these deaths are attributed to abruption of the placenta (placenta prematurely separating from the uterus), placental failure with intrauterine asphyxia (fetus not getting enough oxygen), and extreme prematurity.

The most reliable method of treatment is expedited delivery of the baby. Early diagnosis of this complication is difficult as most of its symptoms are non-specific. Current testing technologies require sending blood samples to the lab when early HELLP syndrome is suspected. By the time results of the test are available, the condition of the patient has already severely deteriorated.

One of the key signs of HELLP syndrome is the occurrence of in vivo hemolysis—a condition which occurs when red blood cells (RBCs) are lysed releasing hemoglobin into blood plasma. Free plasma hemoglobin in healthy individuals is 0.001-0.004 g/dL (Giuseppe Lippi, G. C., Emmanuel J. Favaloro, Mario Plebani, "Hemolysis, An Unresolved Dispute in Laboratory Medicine", *In Vitro and In Vivo Hemolysis* 2012). When it reaches a level of 0.01 g/dL, it indicates hemolysis, and during severe hemolytic episodes it can exceed 1 g/dL. (Rother, R. P., et al., "The clinical sequelae of intravascular hemolysis and extracellular plasma hemoglobin: A novel mechanism of human disease", *JAMA,* 2005. 293(13): p. 1653-1662. Rosse, W. F., "Paroxysmal nocturnal hemoglobinuria-present status and future prospects", *West J Med,* 1980. 132(3): p. 219-28). The increase of hemoglobin concentration in blood above 0.01 g/dL is extremely dangerous, and by the time it reaches 0.1 g/dL the condition of the patient deteriorates so significantly that HELLP syndrome becomes obvious and immediate reaction is needed for saving the patient's life. Presence of high concentration of hemoglobin in plasma results in multiple organ failure and potentially death.

Blood testing is the most frequently performed medical procedure, and the number of blood tests in the US is measured in hundreds of millions per year. Several percent of those tests have to be repeated because of in vitro hemolysis—disruption of the red blood cells and release of hemoglobin and other intercellular content into plasma. Hemolysis is generally detected via visual assessment of plasma, but this is very inaccurate (see FIG. 7, where hemolyzed samples are analyzed visually). Hemolysis cannot be detected in whole blood because of the presence of cells; therefore, centrifugation and plasma separation are required to assess level of hemoglobin in plasma. This can introduce critical delays that can potentially result in death. Additionally, in resource-poor environments, sample preprocessing might be impossible because of a lack of access to hematology labs and trained specialists. Still, prompt detection of hemolysis near patient is critical for saving the lives of the mother and the fetus; however, the current technologies do not support such functionality.

Increase in concentration of hemoglobin in plasma results in color change from clear or yellow to red, when the sample is grossly hemolyzed. The visual assessment is very unreliable, does not provide any quantitative information, and may be even more complicated by elevated concentration of other blood components, such as bilirubin. While there are hemoglobin colorimetric assays allowing measurement of hemoglobin concentration from 0.005 g/dL to 0.5 g/dL, they all require sample preprocessing introducing critical delays to hemolysis detection. Current methods of detecting hemolysis only work with blood plasma, require extensive time for sample preprocessing, and must use large instruments on large blood samples (i.e., milliliters of blood), thus making them inapplicable to near patient analysis.

Accordingly, what is needed is a device and methodology that can utilize just a drop of whole blood and be able to promptly and reliably measure hemoglobin concentration in plasma. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF INVENTION

The long-standing but heretofore unfulfilled need for hemolysis detection in whole blood samples is now met by a new, useful, and nonobvious invention.

In an embodiment, the current invention is a system for measuring hemoglobin concentration in a whole blood sample within a short period of time after drawing the sample from a patient or subject. The system include a containment apparatus having a substantially hollow interior defined by sidewalls that are substantially light impenetrable. Included are left and right sidewalls, bottom and top sidewalls, and front and rear sidewalls. The top sidewall is removable/openable to provide access into the interior of the apparatus from a top side of the apparatus. The rear sidewall is capable of receiving an electronic mobile device (e.g., smart phone, tablet, etc.) that has a camera function. A cuvette stand is disposed on the front sidewall within the interior of the containment apparatus. The cuvette stand is configured to receive and hold a cuvette containing the whole blood sample in a position directly opposite from a camera lens of the mobile device when the mobile is inserted into the rear sidewall.

A computer-based software program is implemented on the mobile device. In the software program, an image of the whole blood sample is received from the mobile device camera. The color of the separated plasma component of the sample is detected, and a hemoglobin concentration and a hemolysis level is automatically determined based on the detected color of the plasma. Thus, when the top sidewall is closed and the mobile device is inserted into the rear sidewall, unwanted external light cannot penetrate into the interior of the containment apparatus.

Hemoglobin concentrations and hemolysis levels may be determined by comparing the detected color of plasma to a set of predetermined red/yellow calibration values built into the software program.

The mobile device may further include a display function, so that the results of determining hemoglobin concentrations and hemolysis levels can be displayed on the mobile device.

The rear sidewall can be a full sidewall or a frame. When it is a full sidewall, a slot would be formed along an outer surface of the sidewall for receiving the mobile device. In this case, the sidewall would include a camera aperture in alignment with the camera lens when the mobile device is inserted into the slot. When the rear sidewall is a frame, is it notched and configured to receive the mobile device so that the mobile device forms a part of the sidewall when inserted into the frame.

A flash dispersing flange or a perforated section may be positioned along the rear sidewall corresponding to a flash of the mobile device camera in order to scatter any light coming from the flash during image capture.

The cuvette stand may include a frame and aperture, where the aperture is configured to receive the cuvette and the frame is configured to hold the cuvette in place during image capture of the whole blood sample.

The front sidewall may have a light-colored inner surface (inside the interior of the containment apparatus) to provide a background against which the image of the sample can be captured.

In a separate embodiment, the current invention is a method of measuring hemoglobin concentration in a whole blood sample within a short period of time after drawing the sample from a patient or subject. A containment apparatus provided having a substantially hollow interior configured to enclose the sample, where the apparatus has at least one (1) opening through which a mobile device can capture an image of the sample. A computer-based software program is provided on the mobile device. A lens of the mobile device is positioned through the containment apparatus opening, such that unwanted external light cannot penetrate into the interior of the containment apparatus. The image of the sample is then captured. The software program then receives the sample image and detects a color of the separated plasma component in the sample. Hemoglobin concentration and hemolysis level is then automatically determined based on the detected plasma color.

A set of predetermined red/yellow calibration values may be input into the software program, wherein hemoglobin concentrations and hemolysis levels may be determined by comparing the detected color of plasma to the calibration values.

The containment apparatus may include an open front side that would be positioned against a flat, light-colored background not only to prevent any unwanted light from penetrating into the interior of the containment apparatus but also to provide a background against which the sample image can be captured.

In certain embodiments, the containment apparatus and software program can include any one or more, or all, of the previously described structural and functional characteristics.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIGS. 8A-8B demonstrate significant difference in color for coagulated and uncoagulated samples.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

In an embodiment, the current invention is a system for hemolysis detection, where the system generally includes—individually or in combination—a containment apparatus for holding the blood sample and a software application for analyzing the blood sample. The containment apparatus houses the sample therein, and blocks out any light from penetrating the apparatus and reflecting off of the sample. In conjunction, the software application uses camera color for processing the color of the sample to determine the hemoglobin level in plasma based on the color.

The software application can be implemented on a mobile phone for early detection of a deadly pregnancy complication, HELLP syndrome, that starts unexpectedly and progresses in a matter of hours, resulting in multiple organ failure and even death of both the mother and the fetus. It is an object of the current invention to detect HELLP syndrome in a patient in less than one hour time interval using only the mobile phone-based system and a citrated blood sample.

In order to be able to detect hemolysis in a patient, two general steps must be conducted: (1) separate plasma from the whole blood sample, and (2) measure the amount of hemoglobin in the sample. As contemplated herein, the plasma separation step can be conducted via natural sedimentation of red blood cells to separate plasma from blood. Subsequently, hemoglobin concentration can be measured using a system or a software application implemented on a mobile device. The typical rate of sedimentation is approximately 15-20 mm/hour, though in pathological cases it can be up to 100 mm/hour. In order to measure concentration of hemoglobin, only a very thin layer of plasma (1-2 mm) is needed. Thus, testing can potentially be initiated after approximately 5-10 min of sedimentation of a fresh citrated blood sample.

Figure 1A:
FIG. 1A depicts natural separation of blood plasma (top) from a whole blood sample. b)
Figure 1B:
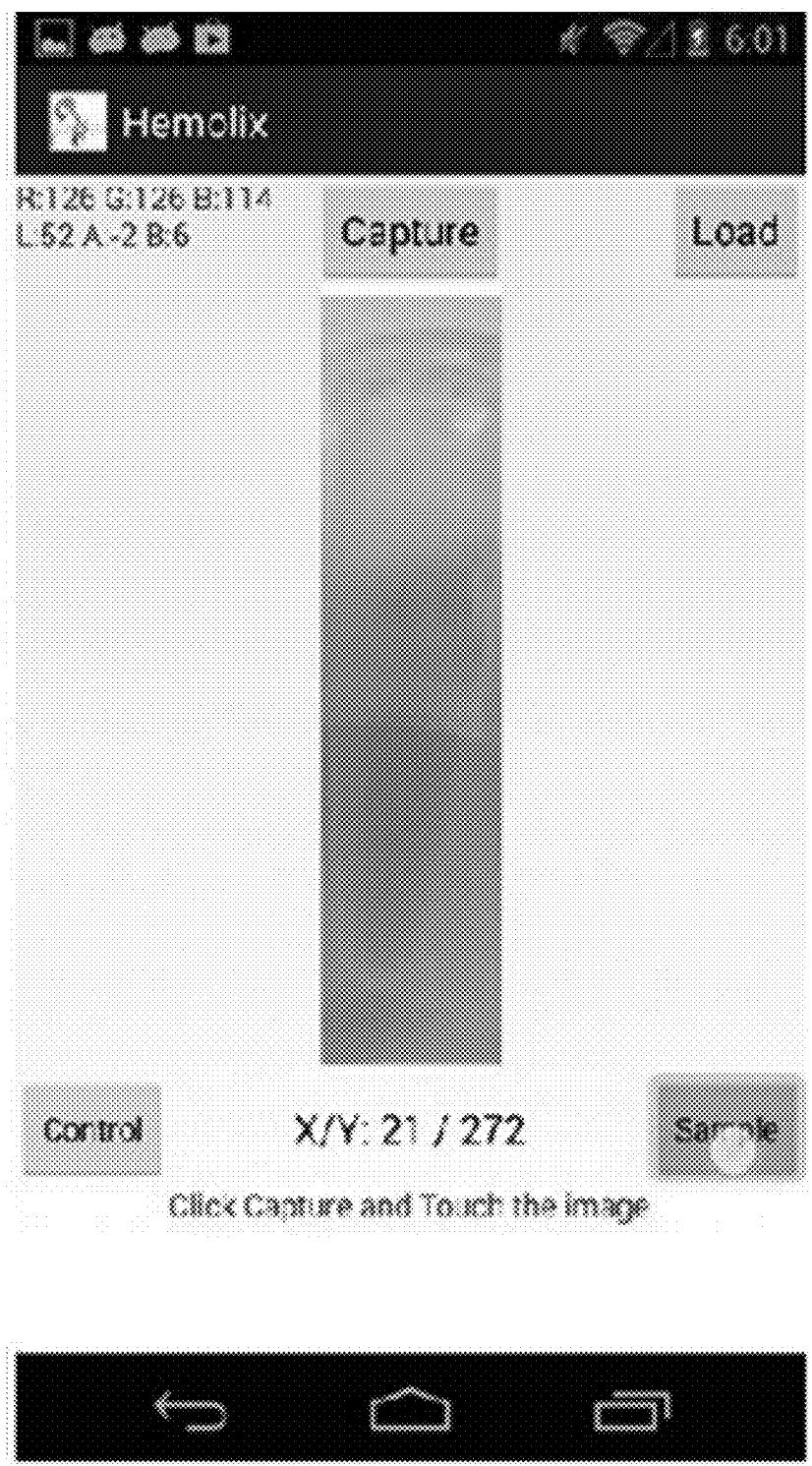
FIG. 1B is a screenshot on a mobile device showing an interface of the software program capturing an image of the settled whole blood sample.
Figure 1C:
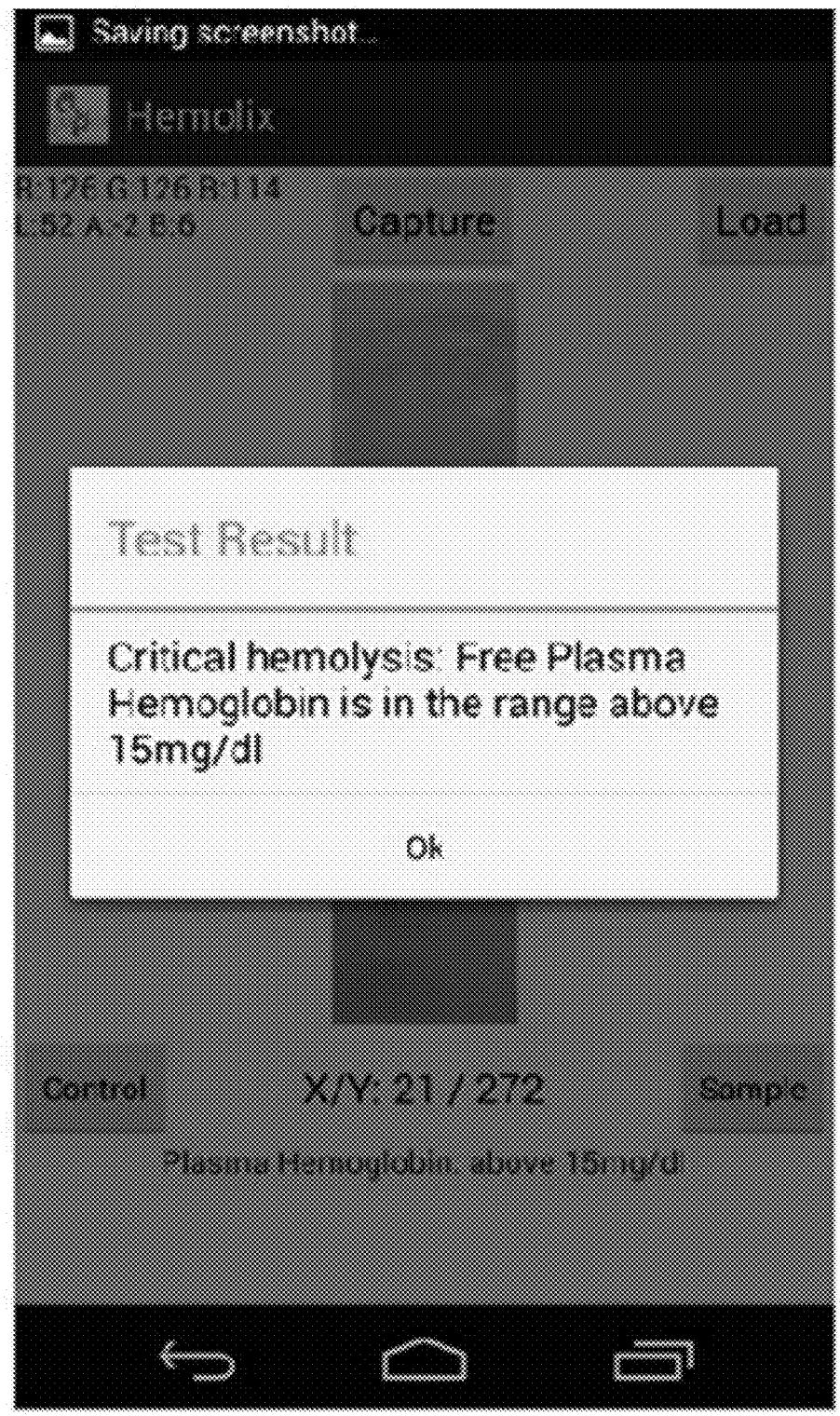
FIG. 1C is a screenshot on a mobile device showing an interface of the software program with the results of the sample analysis.

FIG. 1A shows a whole blood sample after 20 min in a vertical stand. Red blood cells settled down and clear plasma can be seen on top. FIG. 1B depicts an interface on the mobile device for capturing an image of the settled blood sample. FIG. 1C depicts an interface showing results of the sample analysis. The plasma sample is inserted into the containment device, and the camera function on the mobile device is taking an image. The color of the plasma is analyzed by the mobile device and is related to the concentration of hemoglobin, as will become clearer and this specification continues.

Generally, the specifications of performance are as follows, though one of ordinary skill in the art would understand possible variations as contemplated herein. The time needed the sample to be suitable for testing is about 5 to 10 minutes for plasma separation. After the sample is positioned within the containment device, a photo of the sample is taken, and the computer-based analysis is instantaneous. Thus, this early detection of hemolysis can be completed in about 1-2 minutes or less when the plasma has sufficiently settled in the whole blood sample.

At lower concentrations, concentration of hemoglobin can be measured with the precision of about ±1 mg/dL. Lower concentrations can also be detected than would be possible using just a visual assessment. At higher concentrations (very high hemolysis level, >150 mg/dL), the error increases to about ±6 mg/dL. The goal is to determine whether or not hemoglobin concentrations are elevated from a normal level of about 0.001-0.004 g/dL to about 0.01 g/dL and above. The increase of hemoglobin concentration in blood above 0.01 g/dL is extremely dangerous, and by the time it reaches 0.1 g/dL the condition of the patient deteriorates so significantly that HELLP syndrome becomes obvious and immediate reaction is needed for saving the patient's life.

Accuracy

To measure hemoglobin concentration, lab color components are determined for the color of the plasma in the image taken by the camera function on the mobile device. In order to minimize the noise, color is averaged over a square area of 10×10 pixels that completely fits inside of the sample image. Subsequently, a calibration curve is used to find the concentration of hemoglobin that corresponds to the combination of CIELAB color parameters. The calibration curve will become clearer as this specification continues. Alternatively, RGB color parameters can be used.

Figure 2A:
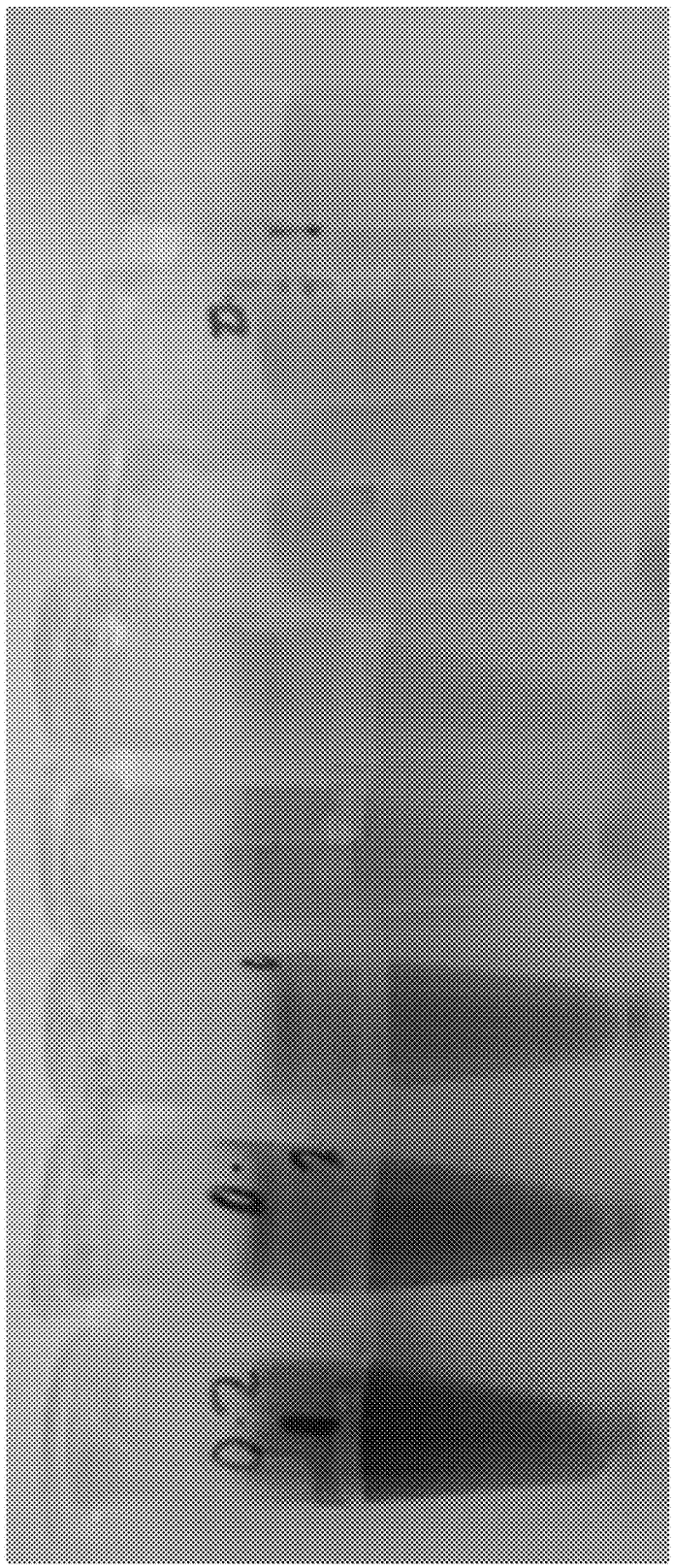
FIG. 2A depicts different concentrations of hemoglobin from about 5 mg/dL to about 200 mg/dL. Pure water is shown in the rightmost sample.

In order to build the calibration curve, multiple concentrations of hemoglobin were prepared in water (FIG. 2A). It should be noted again that free plasma hemoglobin in healthy individuals is about 0.001-0.004 g/dL; concentration of free plasma hemoglobin reaching about 0.01 g/dL and above indicates hemolysis. The lowest concentration used to develop the calibration curve was 0.005 g/dL. The maximum concentration used to develop the calibration curve was 0.2 g/dL, to indicate severe hemolysis. The color difference between pure water and the samples containing hemoglobin was calculated as a square root of the squared differences of three (3) color components:

$$\sqrt{(Li-L0)^2+(ai-a0)^2+(bi-b0)^2}$$

Figure 2B:
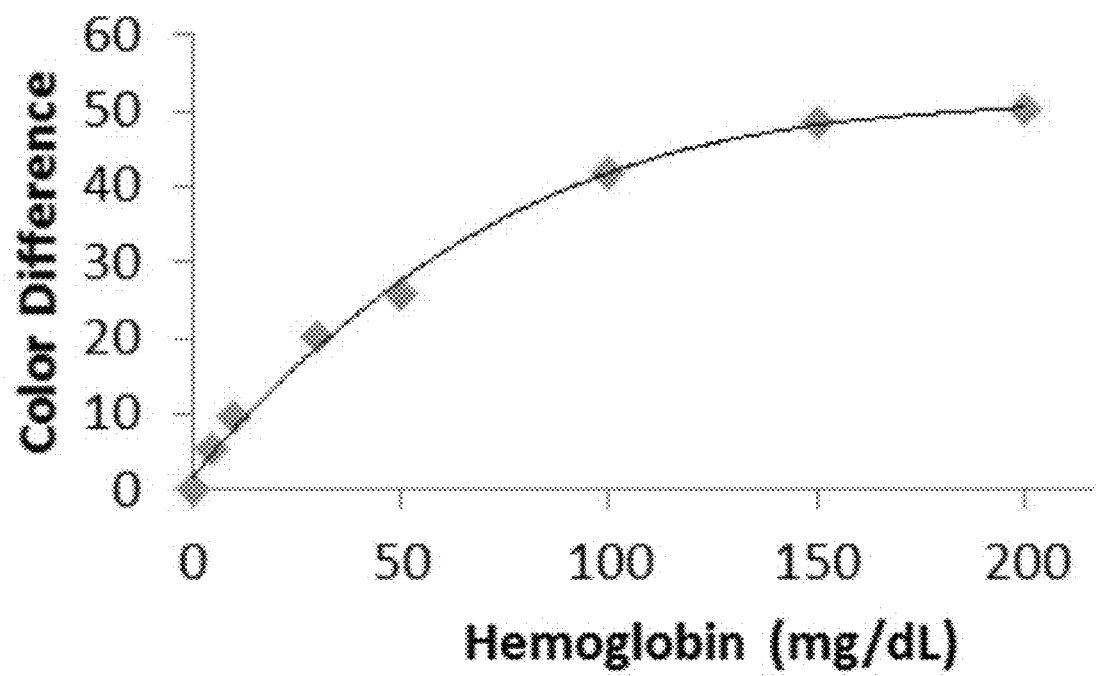
FIG. 2B is a calibration curve showing color difference for the samples with hemoglobin concentration relative to pure water.

FIG. 2B shows the calibration curve, depicting calculated color difference for the different concentrations of hemoglobin, which demonstrates that different hemoglobin concentrations can be clearly distinguished. The calibration curve can be adequately fitted by exponential function similar to Beer-Lambert's law for light absorption. According to Beer-Lambert's law, light absorption exponentially increases with concentration of hemoglobin; in the current color based metrics, color difference increases in a similar way with concentration of hemoglobin.

Several levels of testing were performed to increase accuracy of the camera based color detection.

To test accuracy of the same color at slightly different light conditions, experiments were conducted, taking images of the same sample every 100 seconds and then calculating error of the color difference that was slightly dependent on change in light, minor vibrations, etc. On average, error for the same object photographed six (6) times was between about 0.38 and about 1.48 units. This means that at lower concentrations, hemolysis levels can be measured with precision of about ±1 mg/dL, while at higher concentrations (more than 150 mg/dL) accuracy reduces to about ±6 mg/dL.

Figure 3A:
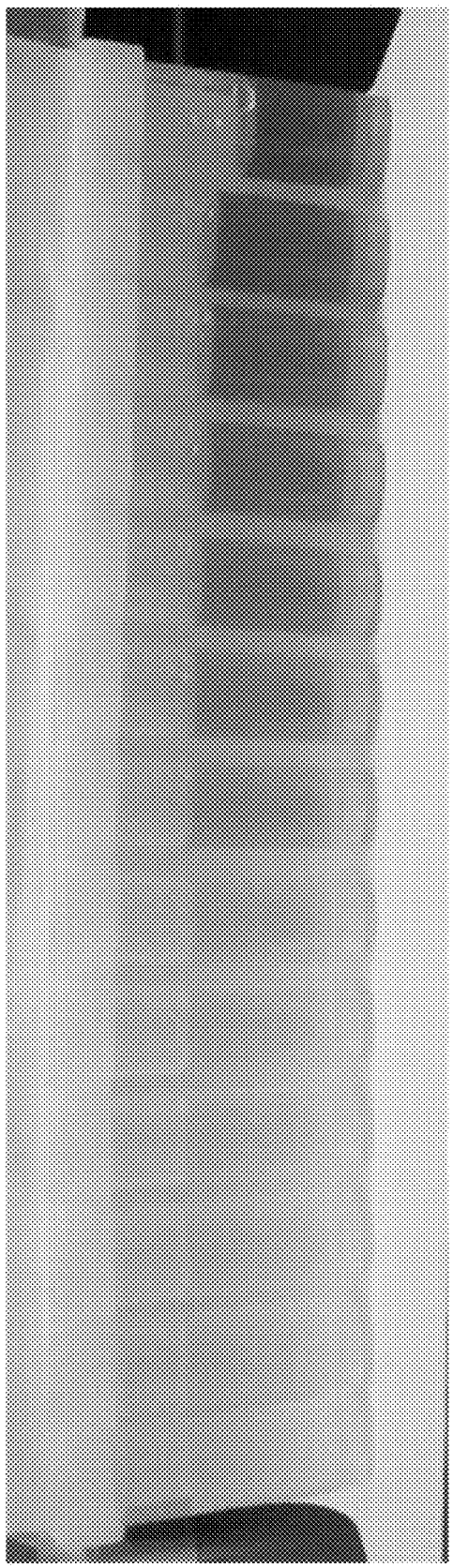
FIG. 3A depicts a set of mixtures of yellow and red dye solutions.
Figure 3B:
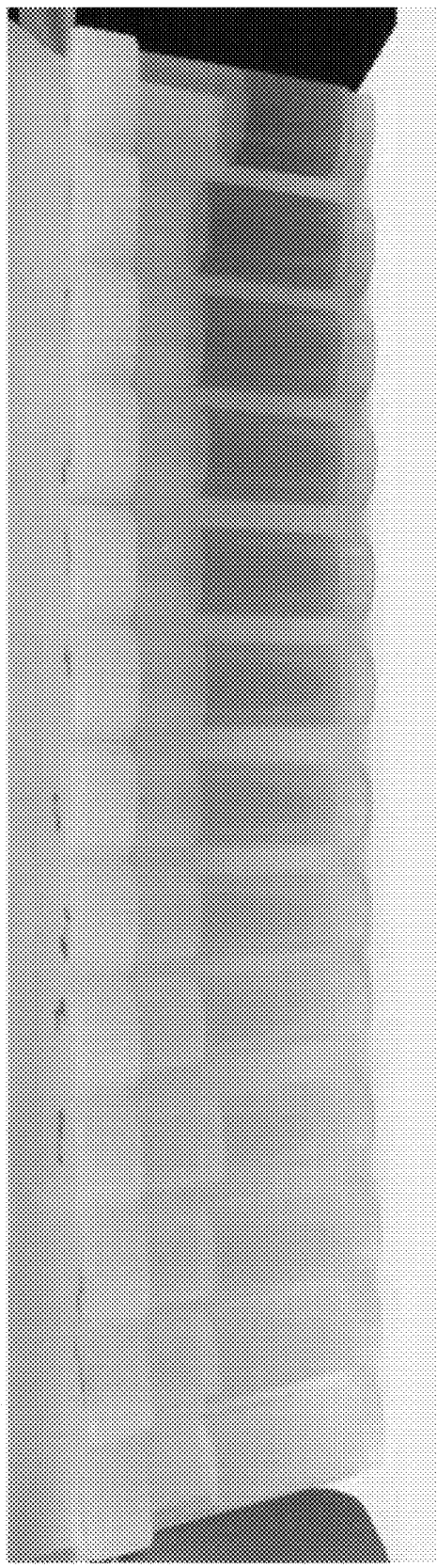
FIG. 3B depicts a set of mixtures, similar to FIG. 3A, but has higher concentration of yellow.
Figure 3C:
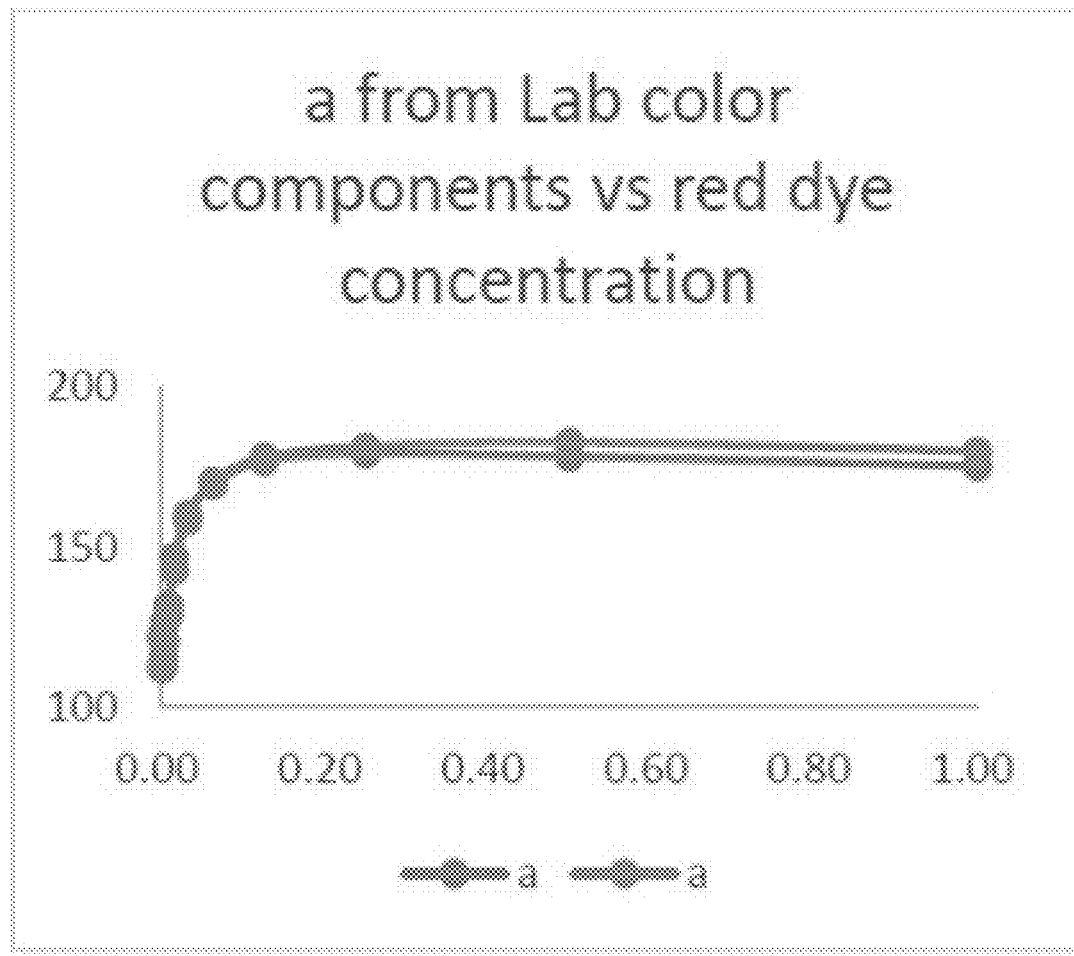
FIGS. 3C-3D are lab color components plotted for two sets of yellow/red mixtures.
Figure 3D:
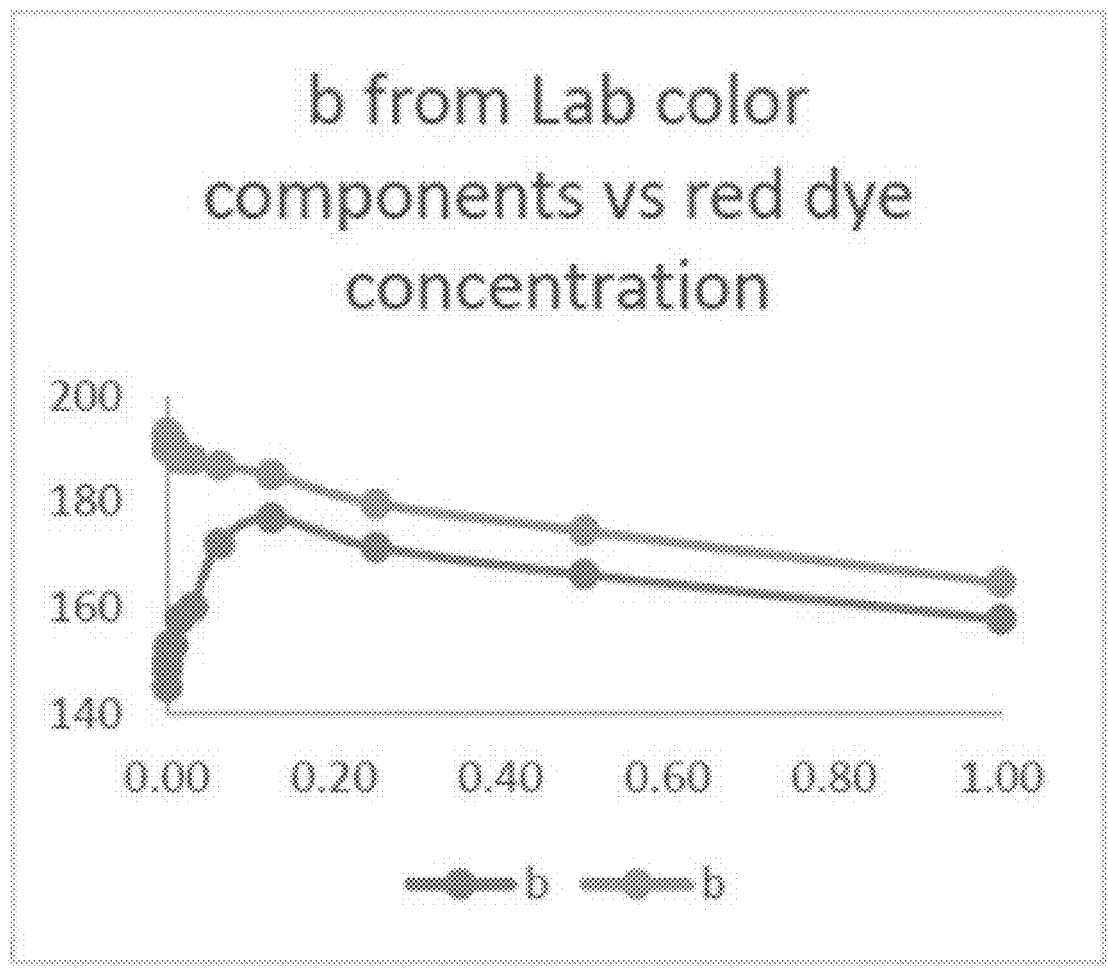

Even without hemoglobin, plasma can have different colors depending on amount of bilirubin (giving the hemoglobin-free plasma a different level of a yellow color). Thus, the method for measuring the accuracy of the hemoglobin measurement can work for different base levels of yellow. For this experiment, three (3) sets of fluids were prepared using two (2) different food colors—red and yellow. Three (3) stock solutions of yellow were prepared with the concentration of the yellow dye 50 µg/dL, 100 µg/dL, 500 µg/dL. Additionally, stock solution of a red dye (20 µg/dL) were prepared. Then for each yellow base, thirteen (13) samples were prepared. Each of them was a mixture of that base yellow color with the same red color solution with twelve (12) concentrations ranging from 3500:1 to 1:1 compared to pure red stock solution. FIGS. 3A-3B shows two sets of fluids for the lowest and the highest concentrations of yellow. FIG. 3C demonstrates that the red color concentration can be tracked using a component of CIELAB colors, while yellow is better monitored with b component (compare FIG. 3C to FIG. 3D). Overall it was found that yellow and red concentrations can be split and tracked independently using several color components, allowing for increased accuracy in hemoglobin concentration measurements.

Mobile Application

The input of the blood sample is from the camera function of a mobile device. The results are shown on the display function of the mobile device (e.g., smart phone, tablet, etc.), optionally saved in the memory or external storage, and e-mailed for further analysis, if needed.

Figure 4:
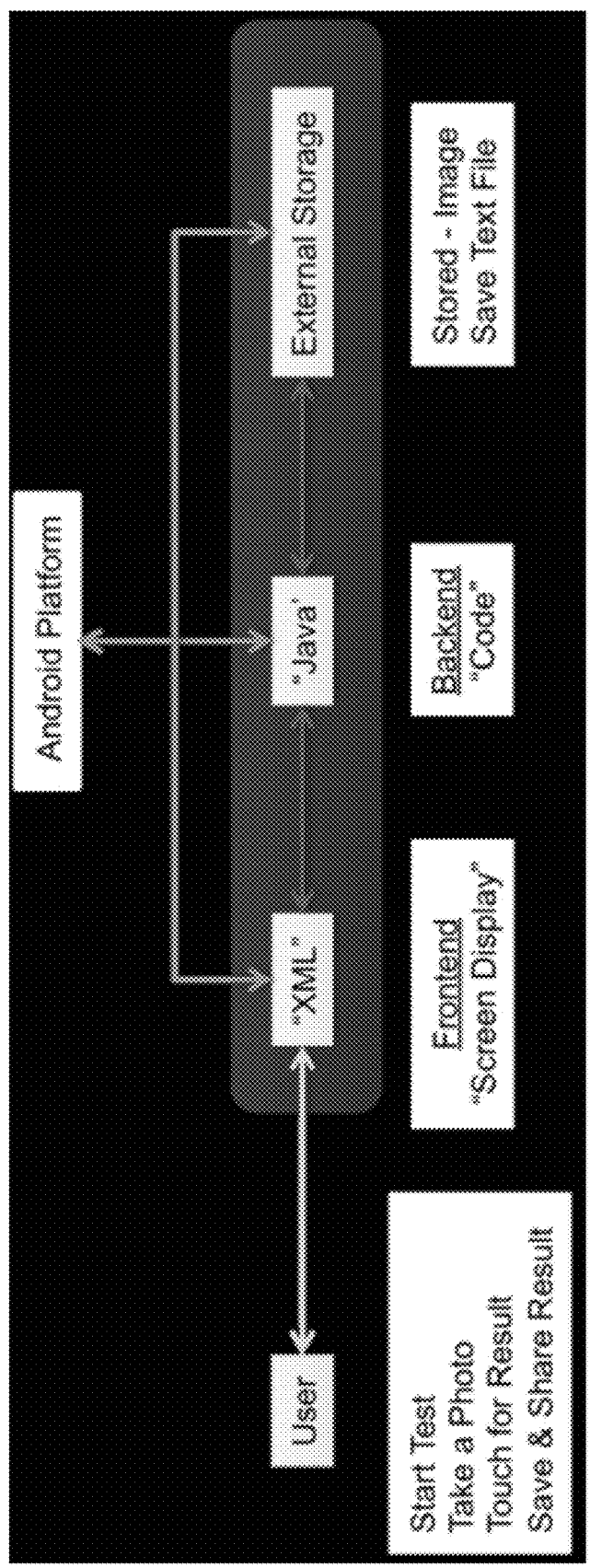
FIG. 4 illustrates exemplary schematics of the working cycle of the software application, according to an embodiment of the current invention. For example, the user starts the application that internally works with Java, XML, and external storage to perform one full cycle of testing. The sample is manually inserted into sample holder, the image is taken via user input, and a reading of the color components is performed, and a calculation of hemolysis level is completed. Information is automatically stored in XML. If needed, images and other information can be stored externally or e-mailed.
Figure 5:
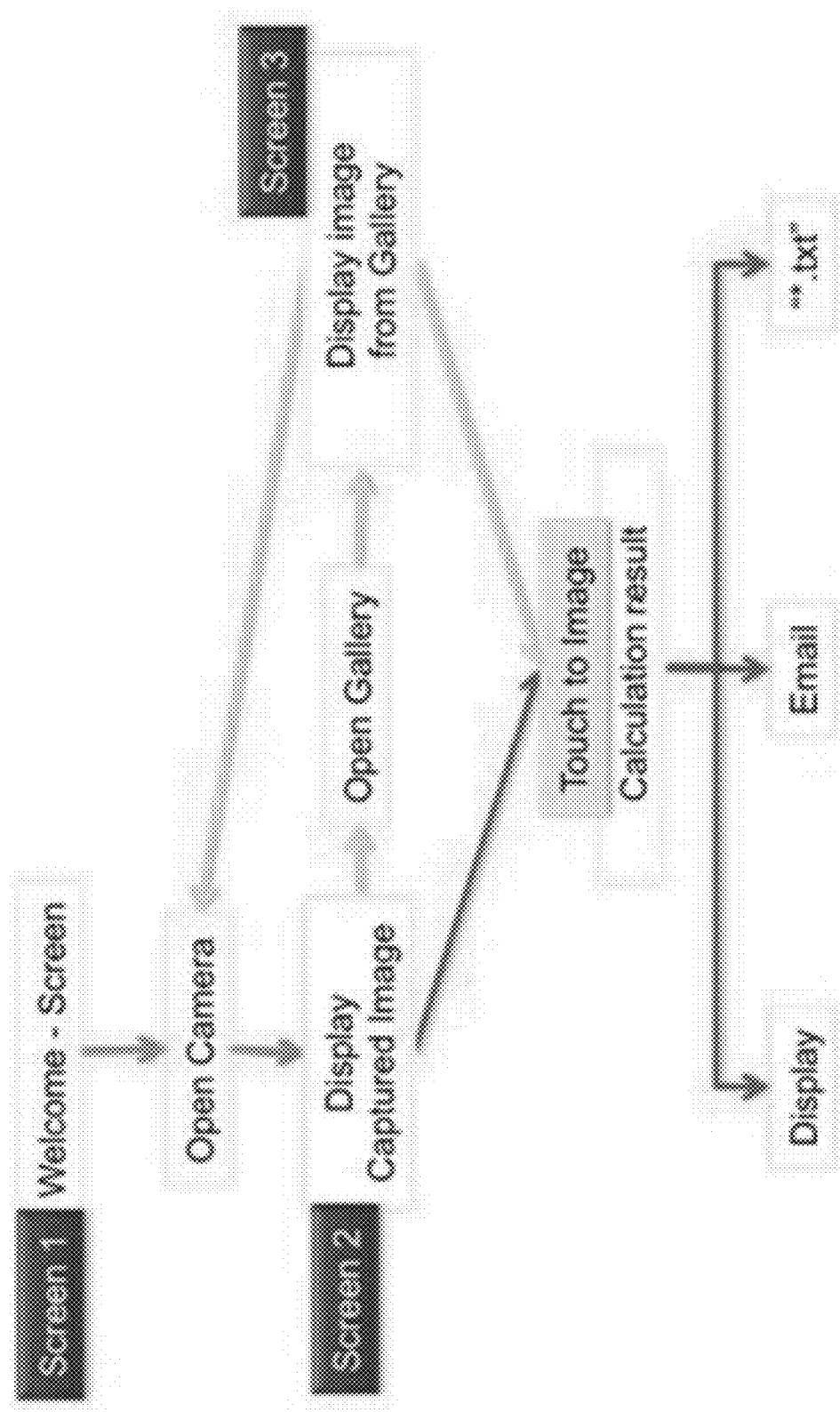
FIG. 5 is a flowchart depicting the logical structure of the mobile application, according to an embodiment of the current invention.

A schematic of the software application can be seen in FIGS. 4-5. The application begins with the welcome screen. The camera is activated, and an image of the blood sample is captured. The application detects the color of the sample and/or plasma component contained therein. The application then analyzes that detected color by comparing the detected color to the calibration values previously formulated and built into the application. This analysis can then use this comparison to determine hemoglobin concentration/levels in the sample and determine hemolysis level. The measurement and analysis results can be displayed on the display function, electronically mailed, and/or saved in a file. The application was initially built on an ANDROID platform using JAVA and XML. Only a small amount of blood sample would be needed for an accurate analysis of the color and determination of hemoglobin concentration. About 1-2 mL samples can be tested/analyzed in small cuvettes or test tubes, while testing of small microliter samples (e.g., 1 drop) is typically done in thin capillary tubes. All of these embodiments are contemplated herein by the current invention.

Containment Apparatus

A sample holder and containment apparatus was developed (e.g., via 3D printing) and coupled to a mobile device. The containment apparatus, generally denoted by the reference numeral 10, is depicted in FIGS. 6A-6D. The structure of containment apparatus 10 can be particularly seen in FIGS. 6A-6B, and use of containment apparatus 10 can be seen with mobile device 22. Containment apparatus 10 includes substantially hollow interior 12 defined by a plurality of sidewalls that are substantially impenetrable by light (i.e., allow minimal to no light therethrough). The light-impenetrable sidewalls include left and right sidewalls 14a, front sidewall 14b, bottom sidewall 14c, removable or hinged or otherwise openable top sidewall 14d. Top sidewall 14d can be opened into open top 14d'. Rear sidewall 16 can be present or can be absent but in either case receives mobile device 22.

Figure 6A:
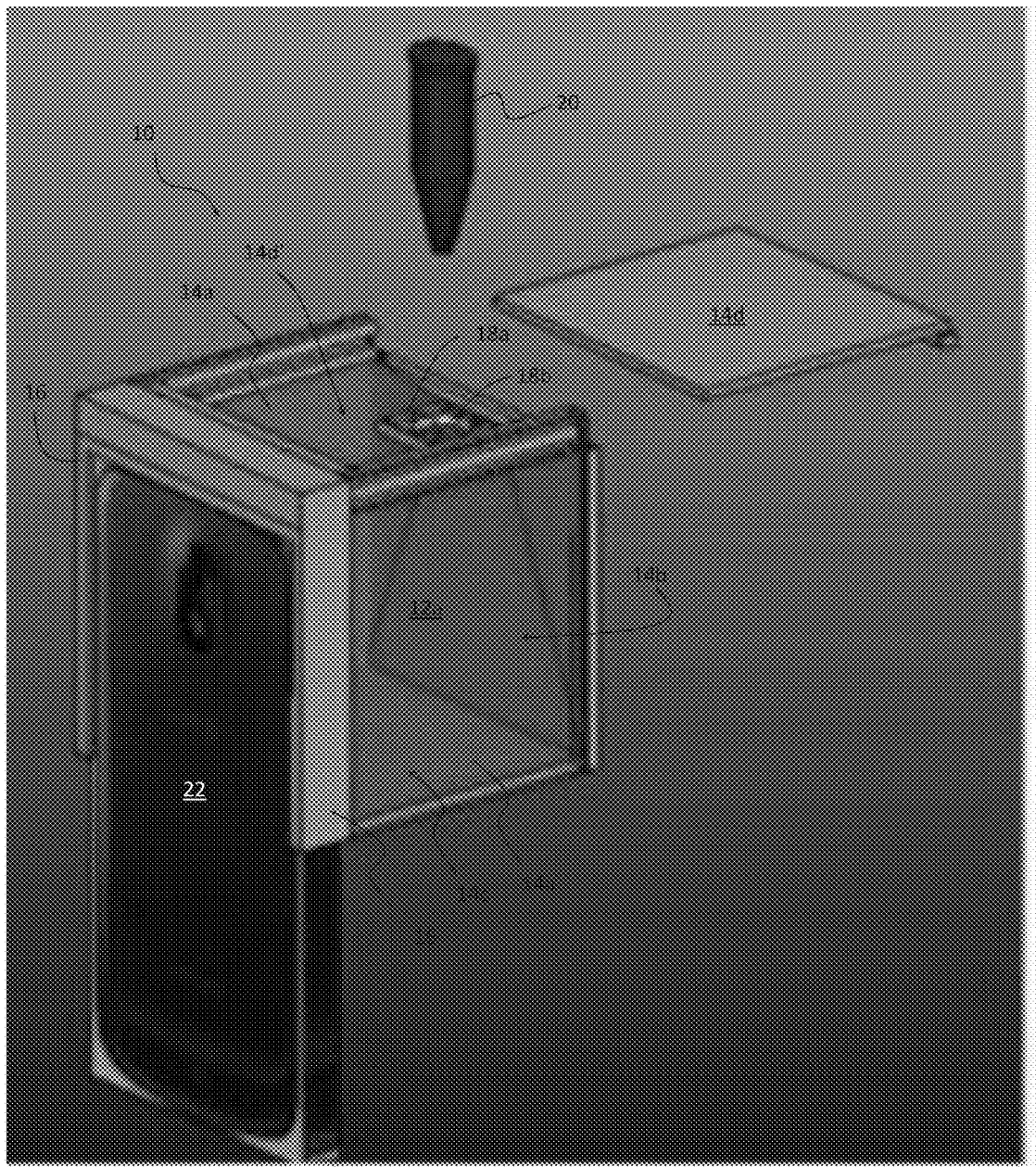
FIG. 6A is a semi-exploded view of a sample holder coupled to a mobile phone, according to an embodiment of the current invention.
Figure 6B:
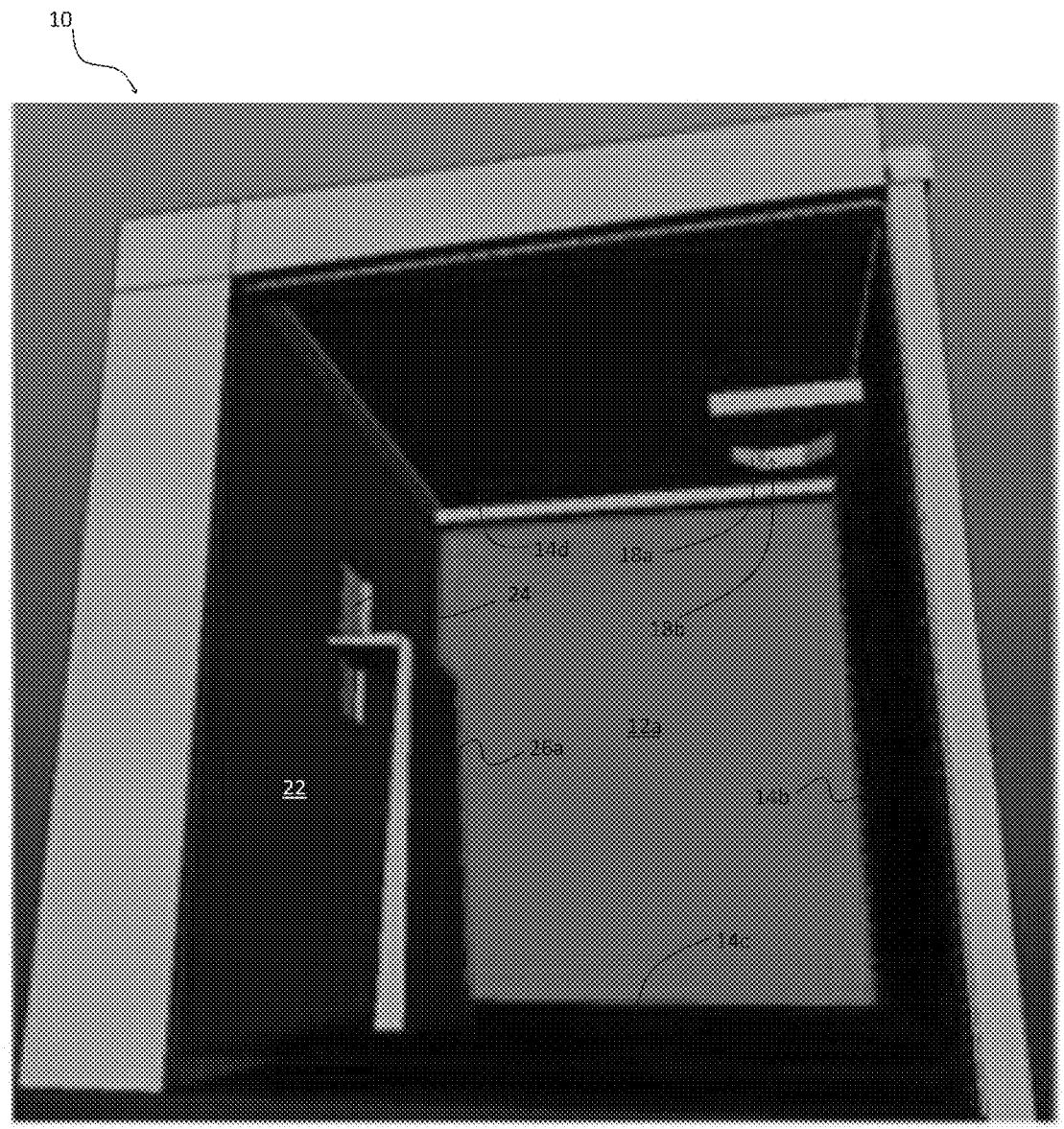
FIG. 6B depicts an interior of the sample holder of FIG. 6A.

If rear sidewall 16 is "absent," as in FIGS. 6A-6B, then rear sidewall 16 would include an outer notched frame for receiving mobile device 22 stably, and mobile device 22 would actually become part of rear sidewall 16, as clearly seen in FIGS. 6A-6B, where FIG. 6A depicts the outer surface of rear sidewall 16 (outer surface of mobile device 22) and FIG. 6B depicts the inner surface of rear sidewall 16 (inner surface of mobile device 22). Mobile device 22 slips into rear sidewall 16.

Figure 6C:
FIG. 6C is a perspective view of an alternate embodiment of the current invention without a mobile device inserted therein.
Figure 6D:
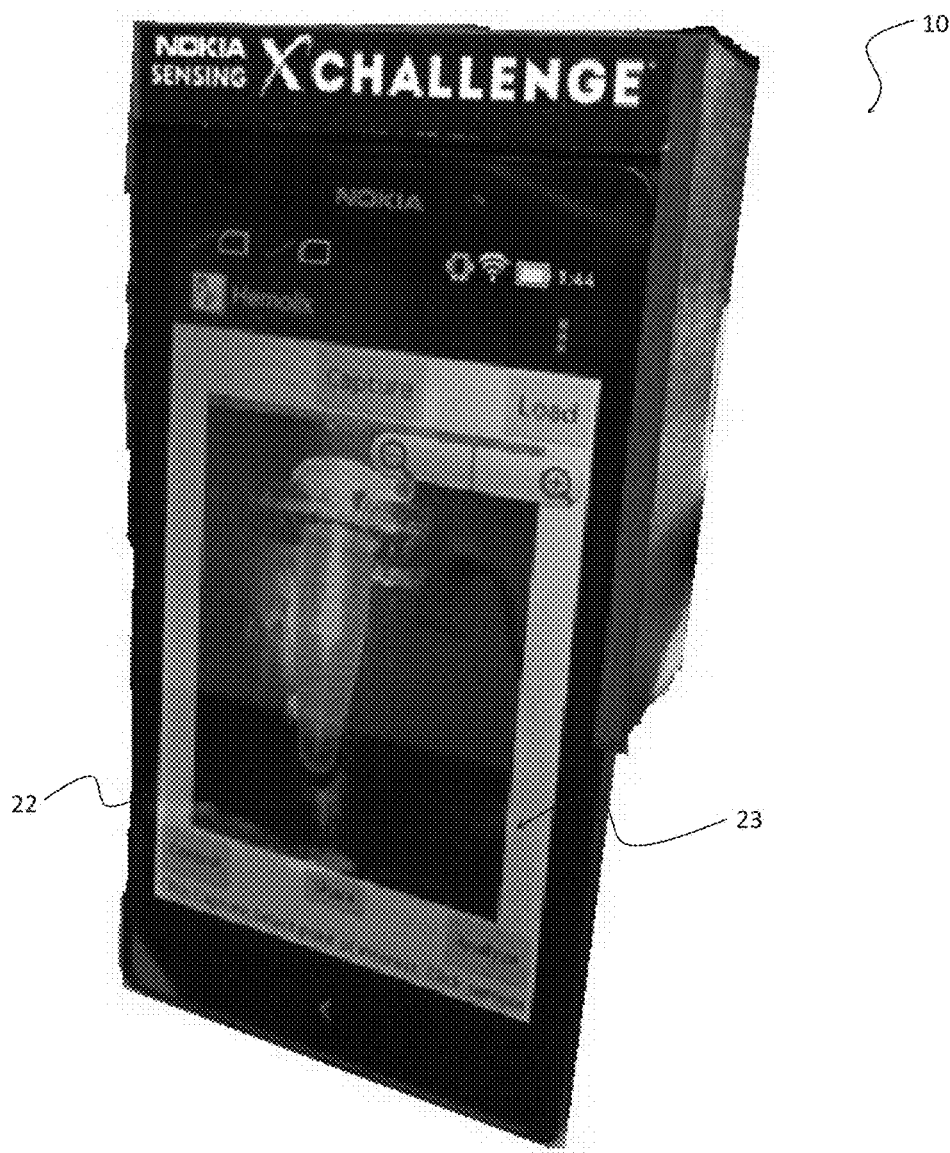
FIG. 6D depicts the embodiment of FIG. 6C with a mobile device inserted therein. The camera function of the mobile device is used for capturing an image of the plasma sample. The information is then processed on the same phone. The display function on the mobile device shows the mobile application with the image of inserted plasma sample.

If present, as in FIGS. 6C-6D, rear sidewall 16 would include a slot, denoted by reference numeral 28, in which mobile device 22 would be inserted. Rear sidewall 16 would also include camera aperture 24 through which the camera function of mobile device 22 can capture an image of the blood sample. Optionally, flash dispersing flange 26 (see FIG. 6B) can be secured to the inner surface of rear sidewall 16 to disperse any light that may be produced from the flash of the camera function of mobile device 22. This would provide better lighting for capturing the image of the blood sample by preventing overexposure of the blood sample. Alternatively, grate or perforated section 26b can be used to scatter the light from the flash of mobile device 22 appropriately.

Top sidewall 14d is removable or openable so as to provide access to substantially hollow interior 12 of containment device 10. In an embodiment, top sidewall 14d is a slidable lid used to close off access to interior 12 via open top 14d'. Within interior 12 of containment device 10 is disposed a cuvette stand formed of cuvette stand frame 18a and cuvette stand aperture 18b, thus combining to form cuvette stand 18a, 18b. Cuvette stand 18a, 18b is structured to receive and hold cuvette 20, so that cuvette 20 can remain stable and in position within interior 12 of containment device 10. Typically, cuvette stand 18a, 18b would be positioned on front sidewall 14b within interior 12 in direct opposition to camera aperture 24 or to where the lens of mobile device 22 would be positioned along rear sidewall 16.

Using the containment apparatus and/or mobile application, according to certain embodiments of the current invention, the current hemolysis diagnostic system is portable, can be integrated into mobile health platforms, and uses standard interfaces.

Methodology in Use

Containment apparatus 10 can be manufactured using any suitable method (e.g., printed using a 3D printer). Mobile device 22 is inserted into and/or becomes rear sidewall 16. Top sidewall 14d opens or is removed to define open top 14d' and provide access to substantially hollow interior 12 of containment apparatus 10. Cuvette 20 containing the whole blood sample with settled plasma is dropped into or otherwise disposed within cuvette stand aperture 18b and stabilized in place using cuvette stand frame 18a.

With cuvette 20 and mobile device 22 secured in place, the blood sample is completely enclosed within substantially hollow interior 12 of containment apparatus 10, in particular via the plurality of light-impermeable sidewalls and mobile device 22, which is also substantially light impermeable. Thus, the blood sample should be contained within a completely pitch-black area without any light entering interior 12 and interfering with the camera function of mobile 22.

At this point, with cuvette 20 enclosed within interior 12 of containment apparatus 10, the camera function of mobile device 22 can be actuated and used to capture an image of the plasma within cuvette 20. That image is taken by or uploaded to the mobile application of mobile device 22. In any case, the image is uploaded to the mobile application and utilizing the foregoing algorithm and calibration curve, the mobile application automatically analyzes the color of the plasma and automatically determines the hemoglobin concentration or hemolysis level of the patient or subject.

Figure 6E:
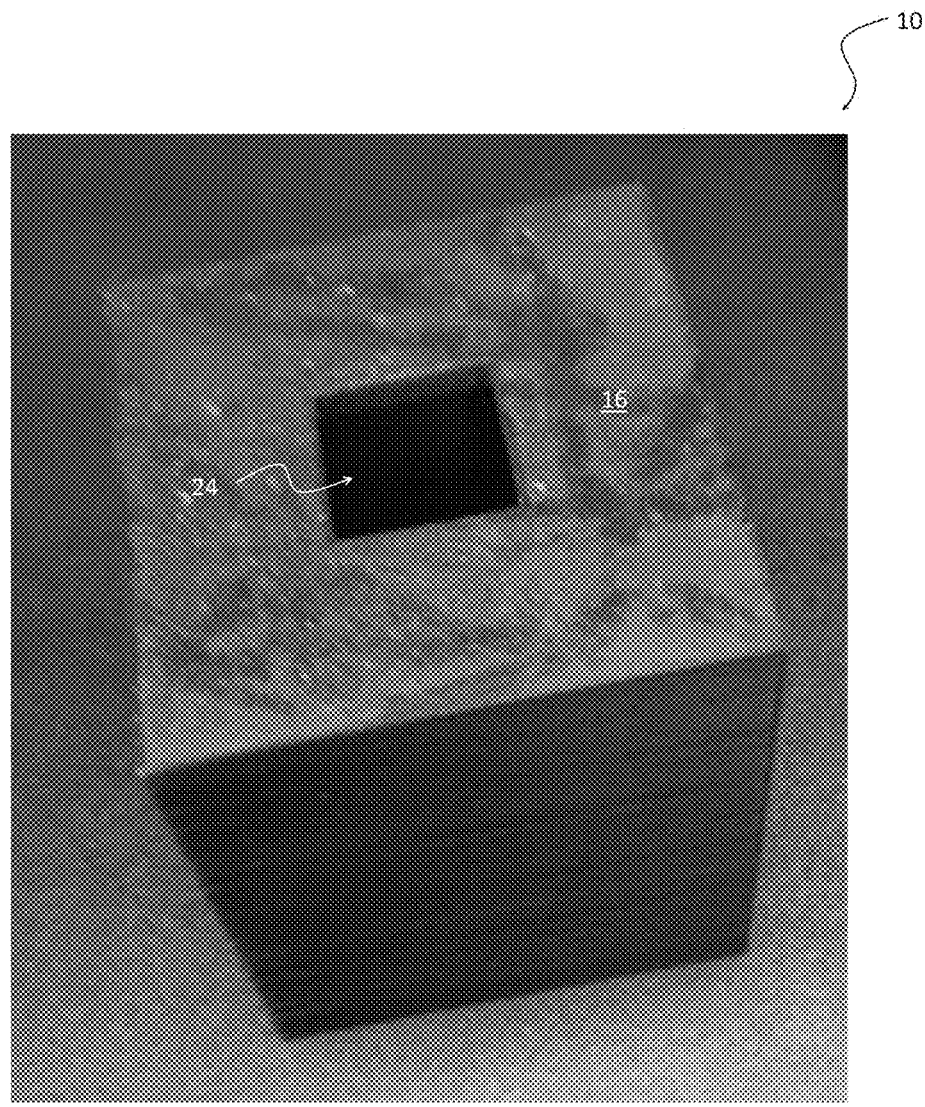
FIG. 6E is a perspective view of an alternate embodiment of the current invention.
Figure 6F:
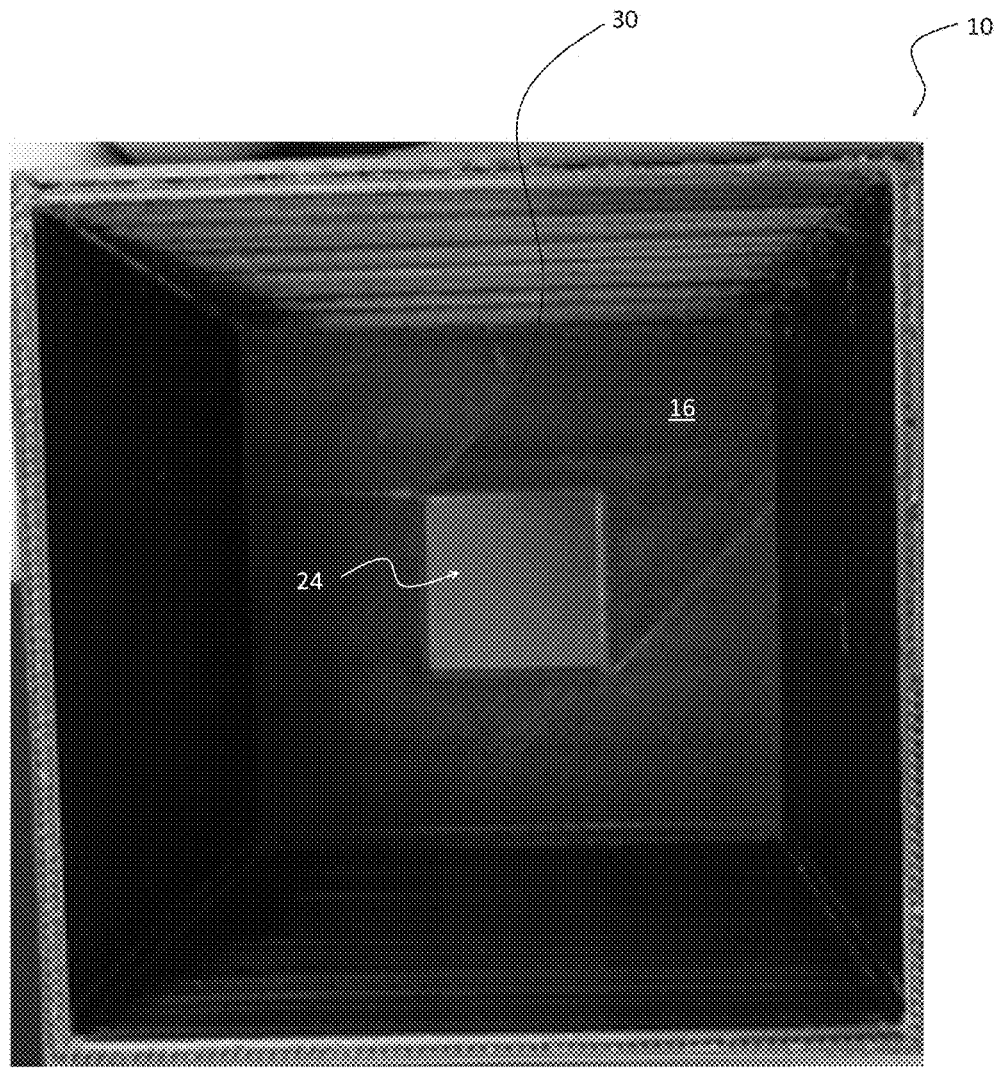
FIG. 6F depicts an interior of the embodiment of FIG. 6E through the open front side.
Figure 6G:
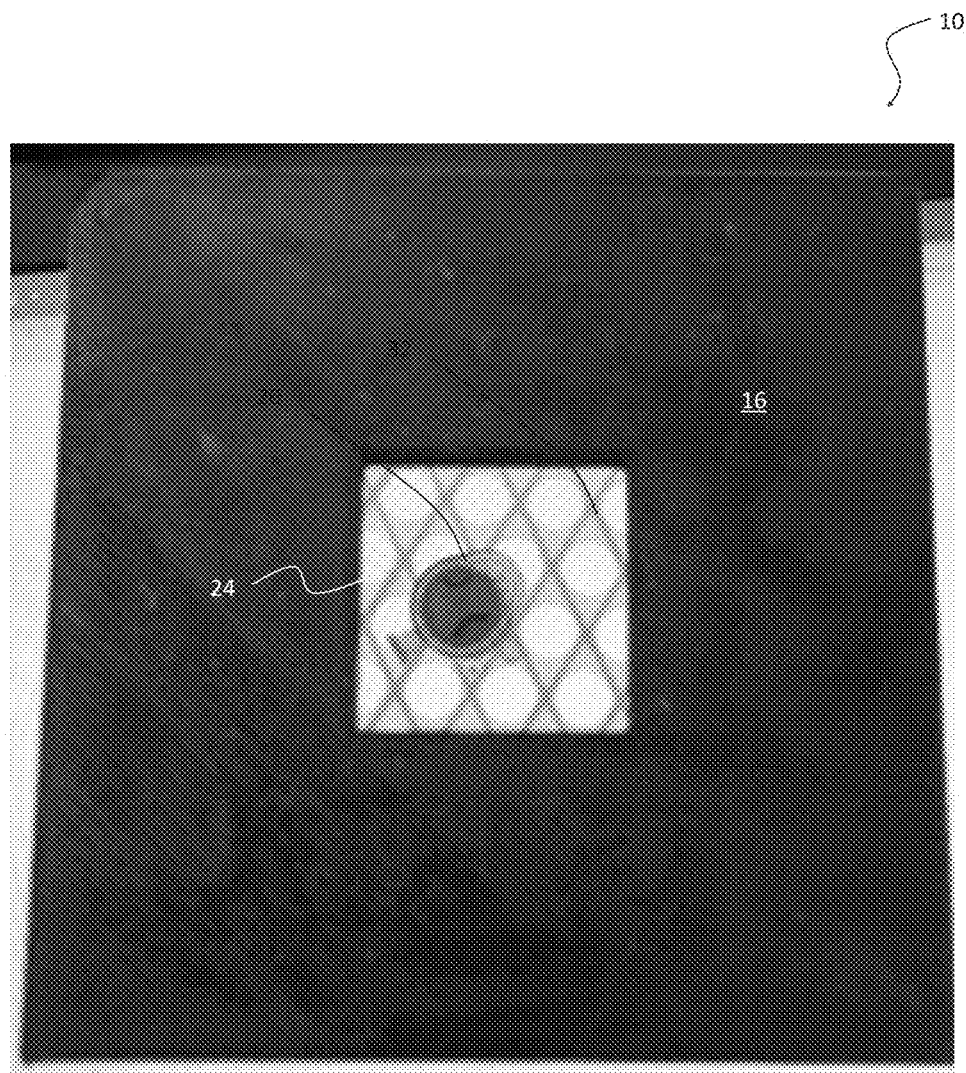
FIG. 6G depicts an interior of the embodiment of FIG. 6E through the camera aperture.
Figure 7:
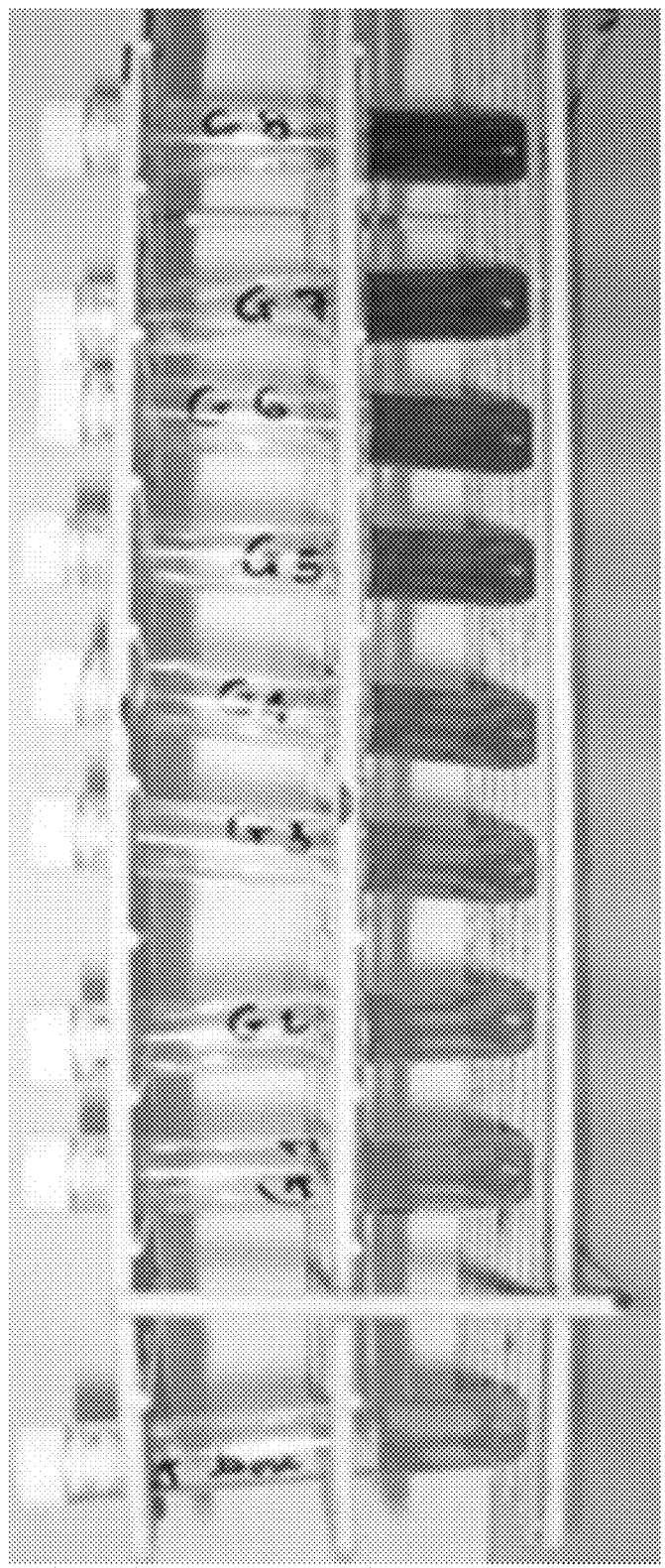
FIG. 7 depicts a conventional visual detection method for hemolyzed samples. From left to right, ranks pure to grossly hemolyzed sample.
Figure 8A:
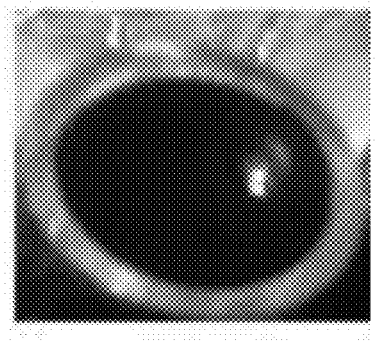
FIG. 8A is an image depicting uncoagulated blood.
Figure 8B:
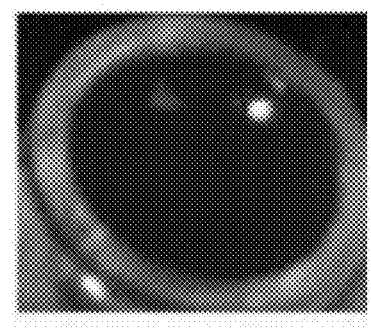
FIG. 8B is an image depicting coagulated blood.
Figure 8C:
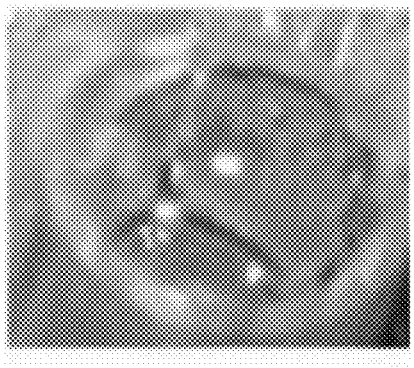
FIG. 8C is an image depicting uncoagulated plasma.
Figure 8D:
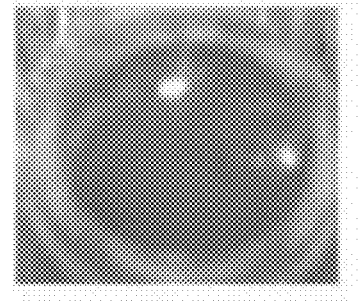
FIG. 8D is an image depicting coagulated plasma demonstrate significant difference in color for coagulated and uncoagulated samples.
Figure 9:
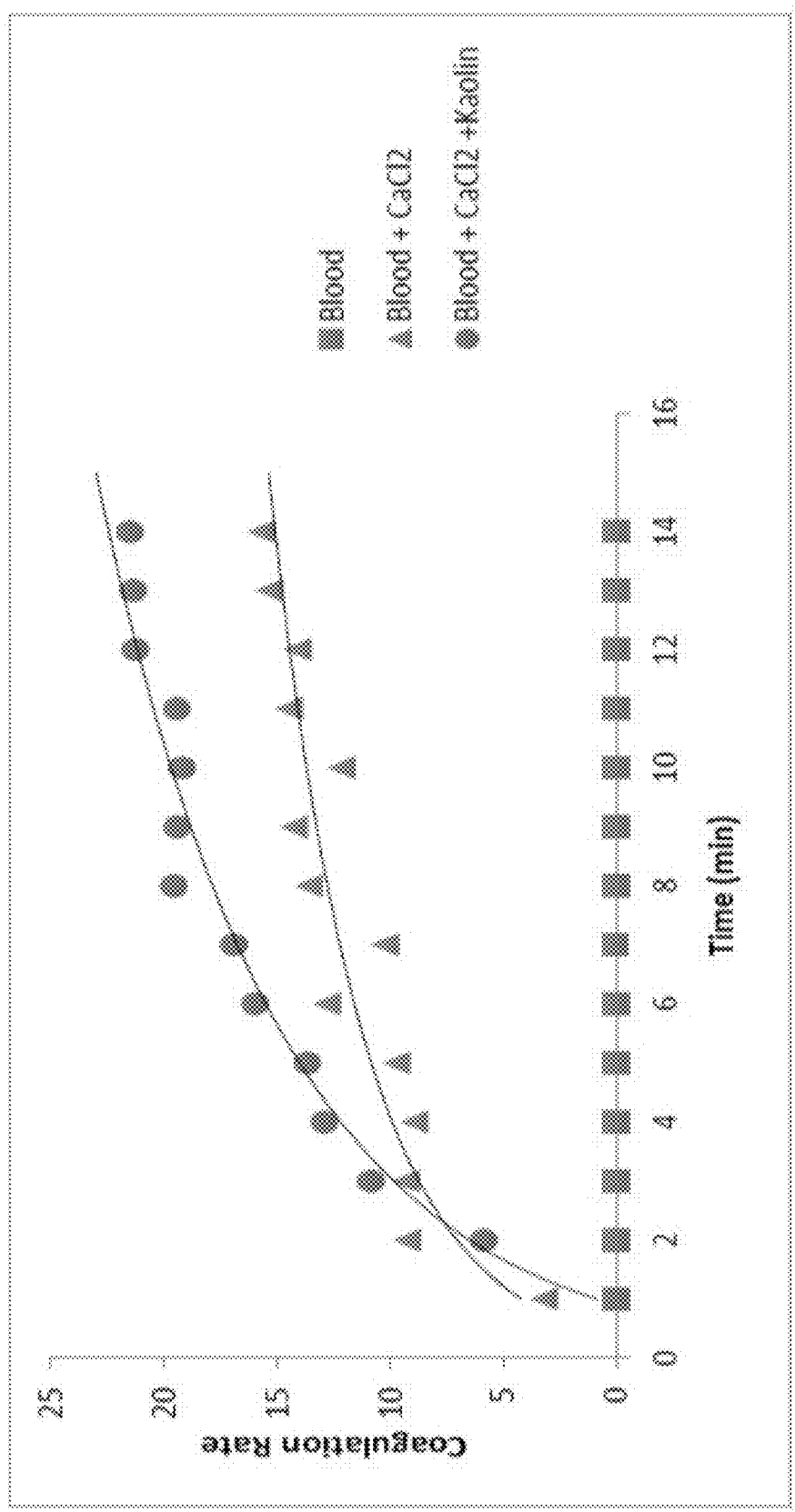
FIG. 9 is a graph depicting continuous tracking of the color change for several coagulating samples. Pure citrated blood does not coagulate. Samples of blood with only $CaCl_2$ and with both $CaCl_2$+Kaolin coagulate, while the latter coagulates faster and forms a stronger clot.

In an alternate embodiment, as seen in FIGS. 6E-6G, containment apparatus 10 includes rear sidewall 16 with camera aperture 24 and open front side 30. In operation, cuvette stand 32 securing cuvette 20 is disposed within open front side 30 and positioned on a flat surface, perhaps with a light-colored background, such as a computer screen. In this position, rear sidewall 16 would typically be facing an upward direction, so that the mobile device camera (not shown in these figures) points downward into containment apparatus 10 through camera aperture 24. The blood sample analysis software program can then be used as described herein to measure hemoglobin concentrations and hemolysis levels.

Multi-Functionality

It is contemplated herein that the current invention can be used in applications beyond measurements and analyses of hemoglobin concentrations and hemolysis levels. For example, the current mobile device-based blood testing platform can be adjusted and calibrated for at least three additional useful applications: (1) in vitro hemolysis detection; (2) near-patient testing of blood coagulation; and (3) measurement of speed of erythrocyte sedimentation. It can also be used as a low cost colorimeter and low cost reader for ELISA and for diagnostic test strips.

In Vitro Hemolysis Detection

While a primary application of the current invention is detection of in vivo hemolysis in blood samples of pregnant women for prompt diagnosis of HELLP syndrome, detection of in vitro hemolysis can be done using a similar system and methodology, since only a blood sample is needed in both cases.

Blood Coagulation

An additional or alternative application of the current invention is a mobile device-based system for detection of speed of blood coagulation. Currently, two (2) million Americans take blood-thinning medications that require visits to the hospital and monitoring of speed of blood coagulation. FIGS. 8A-8D and 10 depict the current system and methodology being tested with blood coagulation (and the results thereof), where change in color of blood and plasma samples was monitored during the coagulation process.

Measurement of Sedimentation Rate of Erythrocytes (ESR)

Measurement of ESR is a simple non-specific screening test that indirectly measures the presence of inflammation in the patient's body. The test indicates the tendency of red blood cells to settle more quickly when a disease is present, typically due to increases in acute-phase reaction proteins. Changes in red cell shape or numbers can also affect the ESR. Thus, an additional image analysis can extract ESR from the image of a sedimenting blood sample.

Hardware and Software Infrastructure Examples

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

GLOSSARY OF CLAIM TERMS

Camera function: This term is used herein to refer to a hardware and software component/module of a mobile device that is capable of capturing and storing an image.

Display function: This term is used herein to refer to a hardware and software component/module of a mobile device that is capable of presenting information to a user thereof.

Electronic mobile device: This term is used herein to refer to any device that is portable and capable of receiving an input, analyzing the input, and transforming the input into an output.

External light: This term is used herein to refer to any visible light that may affect an image of the whole blood sample for an analysis of the color thereof. Typically, this would include light outside of the containment apparatus, though some flash from the mobile device camera may be needed to suitably capture the image of the sample.

Flash dispersing flange: This term is used herein to refer to an extension parallel to an aperture in the rear sidewall of the containment apparatus, where the flange blocks light from the mobile device camera's flash from hitting the whole blood sample too harshly for an appropriate image thereof to be captured. The flange can also simply disperse the light from the flash so that the sample can have an appropriate amount of light for an image thereof to be captured.

Light impenetrable: This term is used herein to refer to a characteristic of a structural component permitting minimal-to-no light to pass therethrough.

Light-colored Inner surface: This term is used herein to refer to white or lighter colored background against which the sample can be photographed. This can be used, for example, if no camera flash is used or insufficient light is produced from the camera flash.

Open front side: This term is used herein to refer to a side of the containment apparatus that permits access from an exterior of the containment apparatus to the interior of the containment apparatus. As such, to close off this side during image capture of the whole blood sample, this "open" side is positioned against a flat surface so that unwanted light does not penetrate into the interior of the containment apparatus.

Perforated section: This term is used herein to refer to an optional integrated or additional component of the rear sidewall of the containment apparatus that is aligned with the camera flash of the mobile device. This section having openings allows light from the camera flash to be dispersed appropriately.

Predetermined red/yellow calibration values: This term is used herein to refer to standards to which a sample's color can be compared to evaluate that sample's red/yellow coloration in order to determine a level hemolysis in that sample. FIG. 2B shows a calibration curve of these standards/values.

Separated plasma component: This term is used herein to refer to a fluid component of whole blood that sits above sedimented red blood cells when a sample containing whole blood is able to settle.

Short period of time: This term is used herein to refer to an amount of time relative to the conventional art where a whole blood sample must be centrifuged and plasma must be separated prior to analysis. Using the current invention, hemoglobin concentration can be measured within about 5-15 minutes after drawing blood from the patient or subject.

Substantially hollow interior: This term is used herein to refer to the interior of the containment apparatus being free of any obstructions or structures that would hinder the goals and objectives of the current invention.

Whole blood sample: This term is used herein to refer to generally unmodified collected blood.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A system for measuring hemoglobin concentration in a whole blood sample within a short period of time after drawing said whole blood sample from a patient or subject, comprising:
   a containment apparatus having a substantially hollow interior defined by a plurality of sidewalls that are light impenetrable,
   said plurality of sidewalls including
   left and right sidewalls,
   a bottom sidewall,
   a top sidewall that is removable or openable to provide access into said substantially hollow interior of said containment apparatus from a top side of said containment apparatus,
   a front sidewall, and
   a rear sidewall or frame that is structured to receive an electronic mobile device having a camera function;
   a cuvette stand disposed on said front sidewall within said interior of said containment apparatus, said cuvette stand configured to receive and hold a cuvette containing said whole blood sample in a position directly opposite from a camera lens of said mobile device;
   a flash dispersing flange positioned along said rear sidewall corresponding to a flash of said camera function of said mobile device in order to scatter any light from said flash,
   wherein said mobile device includes a non-transitory computer medium that contains computer-executable instructions which when executed by a processor causes the processor causes the processor to perform the step of
   receiving an image of said whole blood sample from said camera function of said mobile device,
   detecting a color of a separated plasma component within said whole blood sample, and
   automatically determining a hemoglobin concentration and a hemolysis level in said whole blood sample based on said detected color of said plasma component,
   wherein when said top sidewall is closed and said mobile device is inserted into said rear sidewall, external light cannot penetrate into said substantially hollow interior of said containment apparatus.

2. A system as in claim 1, further comprising:
   said determination of said hemoglobin concentration and said hemolysis level achieved by said computer medium comparing said detected color to a set of predetermined red/yellow calibration values built into said computer medium.

3. A system as in claim 1, further comprising:
   said mobile device further including a display function, and
   said computer medium further including instructions for displaying results of said determination of said hemoglobin concentration and said hemolysis level on said display function of said mobile device.

4. A system as in claim 1, further comprising:
   said rear sidewall or frame being a full sidewall;
   a slot formed along an outer surface of said full sidewall configured to receive said mobile device;
   a camera aperture formed through said full sidewall in alignment with said lens of said mobile device when said mobile device is inserted into said slot.

5. A system as in claim 1, further comprising:
   said rear sidewall or frame being a notched frame configured to receive said mobile device, such that said mobile device forms a part of said rear sidewall when inserted into said notched frame.

6. A system as in claim 1, further comprising:
   a perforated section positioned along said rear sidewall corresponding to a flash of said camera function of said mobile device in order to scatter any light from said flash.

7. A system as in claim 1, further comprising:
   said cuvette stand including a cuvette stand frame and a cuvette stand aperture, said cuvette stand aperture configured to receive said cuvette and said cuvette stand frame configured to hold said cuvette in position for said image to be captured by said camera function of said mobile device.

8. A system as in claim 1, further comprising:
   said front sidewall having a light-colored inner surface to provide a background against which said image of said whole blood sample can be captured.

9. A method of measuring hemoglobin concentration in a whole blood sample within a short period of time after drawing said whole blood sample from a patient or subject, comprising:
   providing a containment apparatus having a substantially hollow interior configured to enclose said whole blood sample, said containment apparatus having at least one (1) opening through which a mobile device can capture an image of said whole blood sample,
   said substantially hollow interior defined by a plurality of sidewalls that are light impenetrable, said plurality of sidewalls including
   left and right sidewalls,
   a bottom sidewall,
   a top sidewall that is removable or openable to provide access into said substantially hollow interior of said containment apparatus from a top side of said containment apparatus,
   a front sidewall, and
   a rear sidewall or frame that is structured to receive said mobile device having a camera function, positioning a flash dispersing flange along said rear sidewall corresponding to a flash of said camera function of said mobile device in order to scatter any light from said flash, providing on said mobile device a non-transitory computer medium that contains computer-executable instructions executed by a processor;

positioning a lens of said mobile device through said opening in said containment apparatus, such that external light cannot penetrate into said substantially hollow interior of said containment apparatus; and capturing said image of said whole blood sample, said processor performing the steps of receiving said image of said whole blood sample from said mobile device, detecting a color of a separated plasma component within said whole blood sample, and automatically determining hemoglobin concentration and hemolysis level in said whole blood sample based on said detected color of said plasma component.

10. A method as in claim 9, further comprising:

inputting a set of predetermined red/yellow calibration values into said computer mediums, wherein said determination of said hemoglobin concentration and said hemolysis level is achieved by said computer medium comparing said detected color to said set of predetermined red/yellow calibration values.

11. A method as in claim 9, further comprising:

said mobile device further including a display function, and said computer medium further including instructions for displaying results of said determination of said hemoglobin concentration and said hemolysis level on said display function of said mobile device.

12. A method as in claim 9, wherein:

a said rear sidewall is structured to receive said mobile device within a slot positioned along said rear sidewall; and the step of positioning said lens of said mobile device through said opening in said containment apparatus is performed by positioning said lens of said mobile device through a camera aperture formed in said rear sidewall when said mobile device is inserted into said slot.

13. A method as in claim 12, further comprising:

positioning a flash of said mobile device through a perforated section positioned along said rear sidewall in order to scatter any light from said flash during image capture.

14. A method as in claim 9, wherein:

a said rear sidewall is formed of a notched frame configured to receive said mobile device, such that said mobile device forms a part of said rear sidewall when inserted into said notched flame.

15. A method as in claim 9, further comprising:

Providing a cuvette stand disposed on said front sidewall within said interior of said containment apparatus, said cuvette stand configured to receive and hold a cuvette containing said whole blood sample in a position directly opposite from a camera lens of said mobile device;

said cuvette stand including a cuvette stand frame and a cuvette stand aperture, said cuvette stand aperture configured to receive said cuvette and said cuvette stand frame configured to hold said cuvette in position for said image to be captured by said mobile device.

16. A method as in claim 9, further comprising:

positioning an open front side of said containment apparatus against a flat, light-colored background to provide a background against which said image of said whole blood sample can be captured.

\* \* \* \* \*